United States Patent
Knorpp et al.

[11] Patent Number: 6,126,442
[45] Date of Patent: Oct. 3, 2000

[54] MOTORISED HANDPIECE

[75] Inventors: Ernst Knorpp; Wolfgang Thaler; Josef Düsing, all of Leutkirch, Germany

[73] Assignee: Kaltenbbach & Voit GbmH & Co., Biberach, Germany

[21] Appl. No.: 09/197,710

[22] Filed: Nov. 23, 1998

[30] Foreign Application Priority Data

Dec. 2, 1997 [DE] Germany ............... 197 53 491

[51] Int. Cl.[7] .................................................. A61C 1/08
[52] U.S. Cl. ..................... 433/126; 433/127; 433/131; 433/133
[58] Field of Search .................... 433/126, 127, 433/129, 131, 132, 133

[56] References Cited

U.S. PATENT DOCUMENTS

| | | | |
|---|---|---|---|
| 2,660,441 | 11/1953 | Toelcke | 433/129 |
| 3,978,586 | 9/1976 | Etherington | 433/131 |
| 4,183,140 | 1/1980 | Rieselman | 433/131 |
| 4,184,256 | 1/1980 | Loge et al. | 433/104 |
| 4,355,977 | 10/1982 | Ota et al. | 433/131 |
| 5,518,398 | 5/1996 | Nakanishi et al. | 433/127 |
| 5,609,445 | 3/1997 | Düsing | 408/124 |

FOREIGN PATENT DOCUMENTS

4406855 A1  9/1995  Germany .

*Primary Examiner*—John J. Wilson
*Attorney, Agent, or Firm*—Marshall, O'Toole, Gerstein, Murray & Borun

[57] ABSTRACT

Motorised handpiece, more particularly for used by dentists or dental technicians, the rotary movement of a motor being transmitted to a tool which can be clamped with the aid of a clamping mechanism. To this end, the rotary movement of the motor is transmitted via an integrally formed shaft to the clamped tool, both the motor and the clamping mechanism being mounted on this integrally formed shaft. As a result of the use of an integrally formed shaft, it is possible to dispense with superfluous ball bearings for mounting the shaft and no mechanical driver system is required in order to couple two separate shafts together, for example.

11 Claims, 5 Drawing Sheets

MOTORISED HANDPIECE

BACKGROUND OF THE INVENTION

1. Technical Field

The present invention relates generally to a motorised handpiece for driving a tool which can be coupled to the handpiece. More particularly, the present invention relates to a motorised handpiece which can be used as a treatment handpiece used by dentists or an operating handpiece used by dental technicians.

2. Background Information

A motorised handpiece for operating a tool which can be coupled to the motorised handpiece, with a motor, with a clamping mechanism for clamping a tool in a force-locking manner, with a shaft arrangement for transmitting a rotary movement of the motor via the clamping mechanism to the clamped tool is known, for example, from DE-A1-44 06 855 and is illustrated in FIG. 5a.

The motorised handpiece 101 illustrated in FIG. 5a essentially comprises two handpiece parts 112, 113, a motor, in the illustrated example a collector-free d.c. motor, being arranged in the handpiece part 112, and a rapid clamping system for a dental tool, for example, being arranged in the other handpiece part 113. The collector-free d.c. motor comprises a short-circuit ring 102, a stator winding 103 and a rotor magnet 104. Current is supplied to the motor via a supply line 118. Furthermore, the rotor magnet 104 is fitted to a first shaft 109, the shaft 109 being rotatably mounted in the handpiece part 112 with the aid of two ball bearings 114, 115. The shaft 109 is thus set in rotation together with the rotor magnet 104 when the motor is actuated.

The rapid clamping system of the second handpiece part 113 essentially comprises a sleeve-shaped, slotted clamping jaw 105, which is arranged coaxially in the said handpiece part and is coupled to or forms part of a further drive shaft 110. At its outer end, the clamping jaw has a conical external shape, which matches a correspondingly shaped conical internal shape of a bearing sleeve 106, in which the clamping jaw 105 is arranged. The clamping jaw 105 is connected or coupled via an actuating mechanism (not shown) to the housing of the second handpiece part 113. The two handpiece parts 112 and 113 can be coupled to one another, more particularly screwed. The two handpiece parts 112 and 113 can be preferably screwed together in the form of a bayonet lock. The above-mentioned actuating mechanism can comprise a starting rod, for example, which upon rotation of the housing of the handpiece part 113 relative to the housing of the handpiece part 112 in a given direction produces an axial displacement of the clamping jaw 105 to the right, the latter being compressed with the increasing longitudinal displacement of the clamping jaw 105 as a result of the matching external and internal shapes of the clamping jaw 105 and the bearing sleeve 106, so that a tool 108, which is located in the clamping jaw 105 and of which only the tool shaft is indicated in FIG. 5a, is clamped in a force-locking manner in the clamping jaw 105. In this respect, the longitudinal displacement of the clamping jaw 105 to the right is effected against a spring force of a spring 107 schematically illustrated in FIG. 5a, which can be a cup or helical spring, for example. A rotation of the handpiece part 113 relative to the handpiece part 112 in the opposite direction accordingly results in a longitudinal displacement of the clamping jaw 105 to the left, which is supported by the spring force of the spring 107. This clamping mechanism is generally referred to as a control grip rapid clamping mechanism. For further details of the clamping mechanism, reference is made to DE-A1-44 06 855.

Of course, the control grip rapid clamping mechanism explained above can also be constructed in such a manner that, instead of the bearing sleeve 106, the clamping jaw 105 is non-displaceably arranged, whilst in contrast to FIG. 5a the bearing sleeve 106 is displaced in the longitudinal direction in synchronism with the rotation of the handpiece part 113 relative to the handpiece part 112.

It can be seen from FIG. 5a that the two handpiece parts 112 and 113 each comprises separate drive shafts 109, 110, which on the one hand are rotatably mounted with the aid of two ball bearings 114, 115 and 116, 117 respectively and on the other hand are coupled to one another via a mechanical driver system 111.

However, in the motorised handpiece shown in FIG. 5a there is a markedly increased production of noise in particular at high rotational speeds on account of unavoidable alignment errors resulting from the mechanical coupling of the two drive shafts 109, 110. Furthermore, a total of four ball bearings 114–117 is required for this motorised handpiece, which limit the rotational speed, in particular in cases where collector-free d.c. motors without additional cooling fans are used. However, it is desirable to dispense with additional cooling fans on account of the desired noise reduction. The maximum rotational speed threshold of the motorised handpiece shown in FIG. 5a for acceptable noise and heat generation is presently approximately 40,000–50,000 $min^{-1}$.

As a result of the two drive shafts 109, 110 coupled together via the mechanical driver system 111, there is increased wear to the two drive shafts 109, 110 in the region of the driver system 111 over time. Furthermore, increased vibration occurs during operation of the motorised handpiece 101 owing to the relatively low overall rigidity of the shaft arrangement produced by the use of the two separate drive shafts 109, 110. Vibrations of this type can result in the so-called white finger syndrome in the user. In this case, blood is forced away from the finger tips of the user who is holding the motorised handpiece 101 with his finger tips in the region of the motorised handpiece part 113, for example, thus causing the finger tips to become white.

FIGS. 5b shows a further known motorised handpiece, which is marketed by the Applicants, for example, under the name "SF motor spindle type 4010". The motorised handpiece 101 shown in FIG. 5a comprises an integrally formed housing 112, in which a motor, for example a three-phase synchronous motor or a collector-free d.c. motor, is again arranged with a short-circuit ring 102, a stator winding 103 and a rotor magnet 104. As in FIG. 5a, the rotor magnet 104 is also fitted on a drive shaft 106 in the motorised handpiece 101 according to FIG. 5b. This drive shaft 106 is constructed as a hollow shaft and at its tool end has a conical internal shape, which, as in FIG. 5a, matches the conical external shape of the sleeve-shaped, slotted clamping jaw 105. This clamping jaw 105 is again part of a tool clamping system, which is arranged inside the hollow shaft 106. To this end, the clamping jaw 105 is integrally constructed with or coupled to a further drive shaft 110, the drive shaft 110 comprising an external thread 120 at one end, which engages in an internal thread of the hollow shaft 106. When the motor is inoperative, the drive shaft 110 with the clamping jaw 105 can be actuated by a rotary knob 121 arranged on the rear part of the motorised handpiece 101, i.e. can be screwed into or out of the hollow shaft 106 in the longitudinal direction. As a result of the conical external shape of the clamping jaw 105, which is designed to match the conical internal shape of the hollow shaft 106, the clamping jaw 105 is compressed as the clamping jaw 105 is screwed with the drive shaft 110 into the hollow shaft 106, so that a tool 108, which is located in the clamping jaw 105 and of which only the tool shaft is indicated in FIG. 5b, is held in a force-locking manner by the clamping jaw 105. Accordingly, when the clamping jaw 105 is screwed out of the hollow shaft 106, the tool 108 is released again from the clamping jaw 105. The motorised handpiece 101 shown in FIG. 5b is suitable, for example, for motor rotational speeds in the region of 60,000 min$^{-1}$.

The motorised handpiece 101 shown in FIG. 5b has an integral construction and therefore has the advantage that it is only necessary to mount the hollow shaft 106 with the aid of two ball bearings 114, 115. Although the drive shaft 106 is mechanically coupled to the other drive shaft 110 as in FIG. 5a as a result of the screw connection between the internal thread 119 and the external thread 120, no driver system 111 of the type shown in FIG. 5a is required in the motorised handpiece 101 shown in FIG. 5b. Consequently, it is possible to make full use of the clearance provided by the bearings 114, 115 and the motor 102–104 with regard to the rotational speed which can be attained. However, a three-phase synchronous motor is conventionally used for the motorised handpiece shown in FIG. 5b, which requires a cooling fan for efficiency reasons and also in view of the rotational speeds which can be attained. The cooling fan generates a relatively high level of noise, in particular in high rotational speed ranges. In addition, the tool clamping system of the motorised handpiece 101 shown in FIG. 5b is awkward from an ergonomic point of view, since an additional rotary knob 121, which has to be manually actuated, is required in order to clamp the tool 108.

SUMMARY OF THE INVENTION

It is therefore the object of the present invention to provide an improved motorised handpiece, in which the above-described problems of the known motorised handpieces do not occur.

More particularly, it is the object to provide a motorised handpiece which combines the advantages of the known motorised handpieces described above, can be more easily handled, is easy to assemble, economical to manufacture, has a compact design and prevents excessive noise generation even at high rotational speeds.

The above objects are achieved according to the invention by a motorised handpiece for operating a tool which can be coupled to the motorised handpiece, with a motor, with a clamping mechanism for clamping a tool in a force-locking manner, with a shaft arrangement for transmitting a rotary movement of the motor via the clamping mechanism to the clamped tool, characterised in that the shaft arrangement is formed by an integrally formed shaft, on which both the motor and the clamping mechanism are arranged. The above objects are also achieved according to the invention by a motorised handpiece for operating a tool which can be coupled to the motorised handpiece, with an angled housing comprising a first housing section and a second housing section arranged at an angle to the first, with a motor accommodated in the first housing section, with a coupling mechanism accommodated in the second housing section for coupling a tool to the motorised handpiece, and with a shaft arrangement for transmitting a rotary movement of the motor via the coupling mechanism to the tool coupled to the motorised handpiece, the shaft arrangement comprising two shafts coupled to one another via a mechanical transmission mechanism, the first shaft being integrally formed, being arranged in the first housing section and at one end supporting the motor and at its other end supporting the mechanical transmission mechanism, and the second shaft being arranged in the second housing section and being coupled to the coupling mechanism.

Like the initially described motorised handpieces, the motorised handpiece according to the invention according to claim 1 comprises a motor and a clamping mechanism for the force-locking clamping of a tool, although in accordance with the present invention the motor as well as the clamping mechanism are fitted onto the same integrally formed shaft. In principle, it is only necessary to mount this shaft with the aid of two ball bearings, so that the friction losses between the bearings and the shaft as well as the running noises can be reduced. Furthermore, the shaft rigidity of the overall arrangement is higher and wear to the shaft lower than in the case of two shafts coupled to one another. Similarly, the motorised handpiece according to the invention can be constructed in such a manner that it is more compact, easier to assemble and easier to manufacture at reduced cost. Excessive vibrations during operation of the motorised handpiece are avoided as a result of the integrally formed shaft.

In order to keep losses low even at high rotational speeds, the motor output can be minimised. The use of a cooling fan is unnecessary, so that additional noises are not produced as a result. Similarly, no mechanical driver system is required, so that coupling noises can be prevented. The motorised handpiece according to the invention allows for a ball bearing arrangement which in the event of repairs, for example, allows for extremely simple replacement of the individual ball bearings, since the ball bearings are easily accessible from the outside. The motorised handpiece according to the invention can be advantageously combined with the initially described and particularly user-friendly control grip rapid clamping system, the motorised handpiece being constructed in two parts to this end and a tool can be simply clamped by the relative movement of one handpiece part relative to the other handpiece part.

In principle, the motorised handpiece according to the invention can be used for all areas of application where a tool is to be driven so as to rotate. More particularly, however, the motorised handpiece can also be used by dentists or dental technicians, it being possible in this case to use the motorised handpiece on the one hand as a treatment handpiece used by dentists or on the other hand as an operating handpiece used by dental technicians. The use of only one shaft in the core region of a motorised handpiece, is applied to an angled motorised handpiece, as is used in particular by dentists.

The invention will be explained in further detail in the following with the aid of preferred embodiments with reference to the enclosed drawings.

DETAILED DESCRIPTION OF THE PREFERRED EMBODIMENTS

FIGS. 1a–1d show different variants of a first embodiment according to the invention. As will be explained in further detail in the following, according to this first embodiment of the invention the motorised handpiece is constructed in two parts, a clamping system for a tool which is to be driven by the motorised handpiece being arranged in one handpiece part and a motor being arranged in the other handpiece part. The motor and the clamping mechanism are fitted to the same shaft, which is integrally formed. The clamping mechanism for the tool is more particularly constructed as a control grip rapid clamping system, i.e. a tool introduced into the clamping mechanism is automatically clamped in a force-locking manner by rotating the handpiece part associated with the clamping mechanism relative to the handpiece part associated with the motor, so that the rotary movement of the motor is transmitted via the integral shaft to the clamped tool.

Figure 1A:
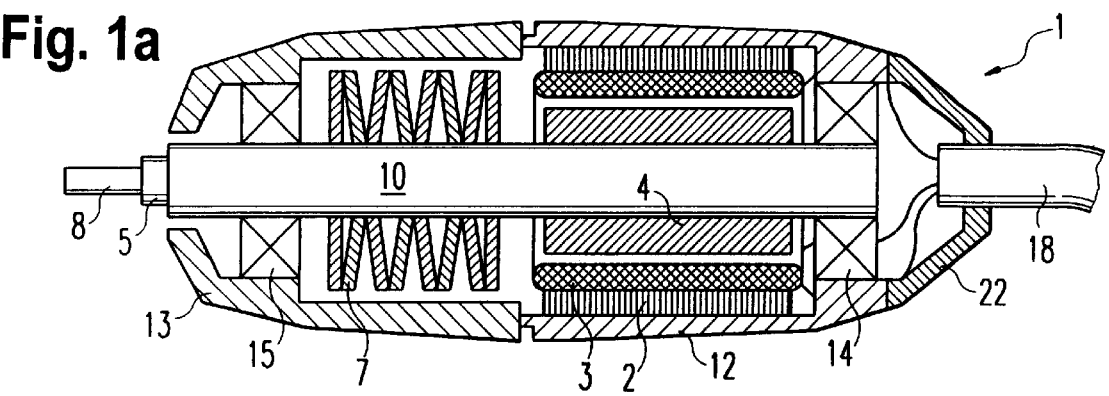
FIGS. 1a–1d show different variants of a first embodiment of a motorised handpiece according to the invention.

FIG. 1a shows a motorised handpiece 1 which is formed by two handpiece parts 12 and 13 which can be coupled together. Arranged in the handpiece part 12 is the already-mentioned motor, which in the illustrated example is constructed in the form of a collector-free d.c. motor with a short-circuit ring 2 made of sheet iron, for example, a stator winding 3 and a rotor magnet 4. The rotor magnet 4 can be a bipolar diametrally magnetised permanent magnet, for example. Like the handpiece part 12, the short-circuit ring 2, the stator winding 3 and the rotor magnet 4 are substantially rotationally symmetrical and each have a cylindrical shape. The rotor magnet 4 is fitted in a force-locking manner onto a drive shaft 10, so that the drive shaft 10 is driven by the rotation of the rotor magnet 4. The collector-free d.c. motor is supplied with current via a supply line 18, the supply line 18 being guided through an opening at the supply line end of the motorised handpiece 1 into the interior of the handpiece part 12. Located at the supply line end of the handpiece part 12 is a ball bearing 14, on which the drive shaft 10 is rotatably mounted. At its supply line end, the handpiece part 12 comprises a removable cover 22, so that the ball bearing 14 is easily accessible from the supply line end of the motorised handpiece 1 and can therefore be simply replaced in the event of repair.

Figure 5A:
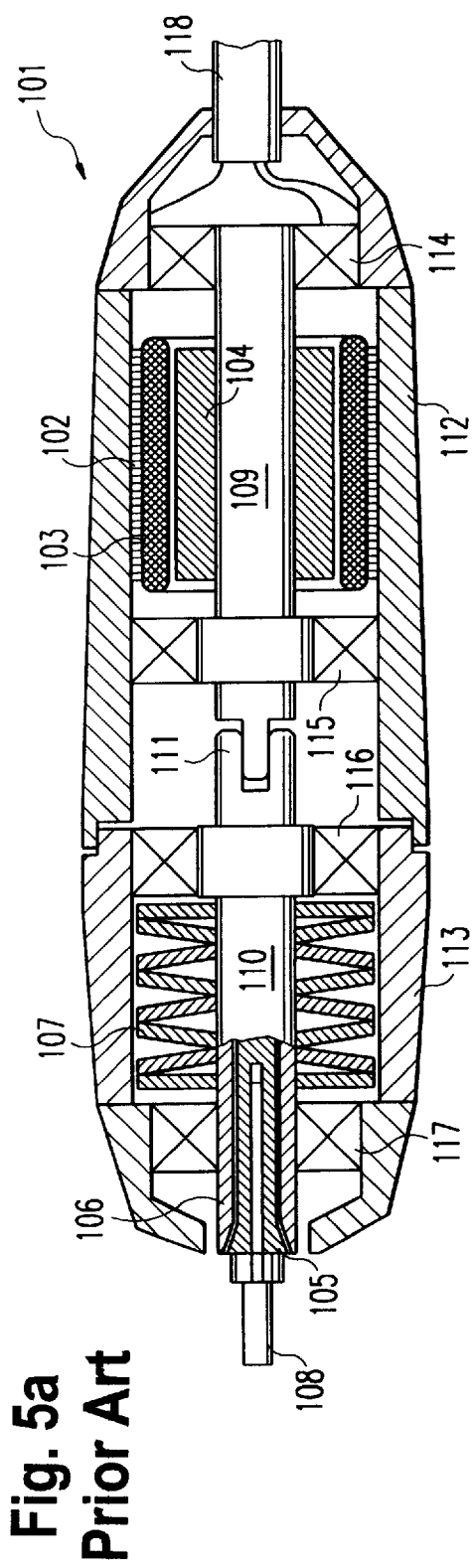
FIGS. 5a and 5b show known motorised handpieces.
Figure 5B:
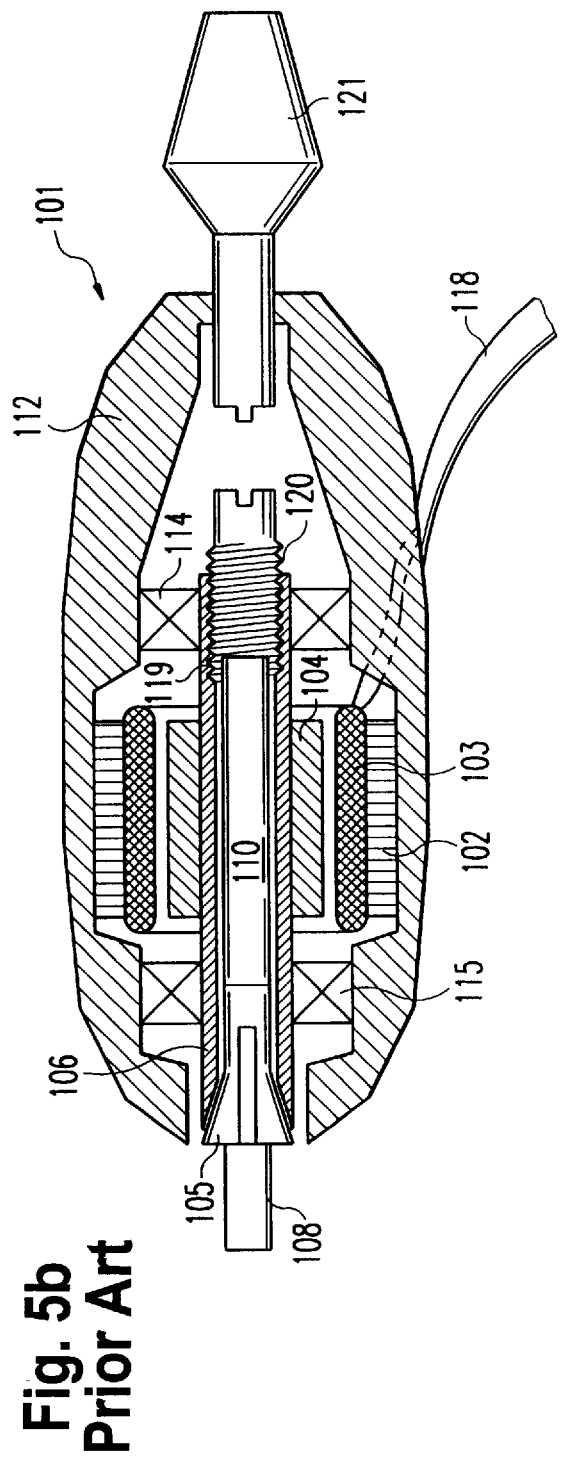

The second handpiece part 13 comprises the already-mentioned clamping mechanism. In the embodiments illustrated in the drawings, this clamping mechanism is constructed as a rapid clamping mechanism as in FIG. 5a. In other words, also provided in the embodiments described below is a clamping jaw 5, for example, which upon rotation of the handpiece part 13 relative to the handpiece part 12 can be displaced in the longitudinal direction relative to the outer casing of the shaft 10, so that a tool 8, e.g. a dental tool, which is disposed in the clamping jaw 5, can be clamped in a force-locking manner simply by rotating the handpiece part 13 acting as a rotary knob. As in FIG. 5a, elastic means 7, more particularly a spring, is again provided, against whose spring force the clamping jaw 5 is moved into the handpiece part 13 and the tool 8 is clamped. As regards the more detailed method of operation of this clamping mechanism, reference is made at this point to the explanations relating to FIG. 5a. Whilst FIG. 5a illustrates a partial cross section of this clamping mechanism, FIG. 1 is merely an external view of the drive shaft 10 with the section of the clamping jaw 5 projecting therefrom and the spring 7. The spring 7 can be constructed, for example, as a cup or helical coiled spring and—as already explained with the aid of FIG. 5a—is coupled to the clamping jaw 5 in such a manner that it is compressed when the clamping jaw 5 is drawn into the handpiece part 13 as a result of a rotation of the handpiece part 13 relative to the handpiece part 12.

As can be seen in FIG. 1a, the drive shaft 10 is also rotatably mounted in the handpiece part 13 at the tool end thereof by means of a ball bearing 15. In all, a single shaft system with only two ball bearings 14, 15 for the entire motorised handpiece 1 is therefore formed, although a rapid tool clamping mechanism (control grip rapid clamping mechanism) is again used.

The collector-free d.c. motor (without position indicator) illustrated in FIG. 1a is constructed in such a manner that the stator winding 3 is associated with the supply line 18 in a fixed or pluggable manner and the rotor magnet 4 is associated with the drive shaft 10 in a fixed or screwable manner. Consequently, a simple division and separation of the entire motor region into the supply line 18 and the motorised handpiece section is possible. Overall, optimal minimisation of the external dimensions and weight of the motorised handpiece is attained with the aid of the motorised handpiece according to the invention. In addition, a bearing replacement can be simply effected in situ with the aid of the single shaft system according to the invention.

Different variants of the motorised handpiece according to the present invention illustrated in FIG. 1a will be described in the following. In this respect, corresponding components are provided with identical reference numerals.

Figure 1B:
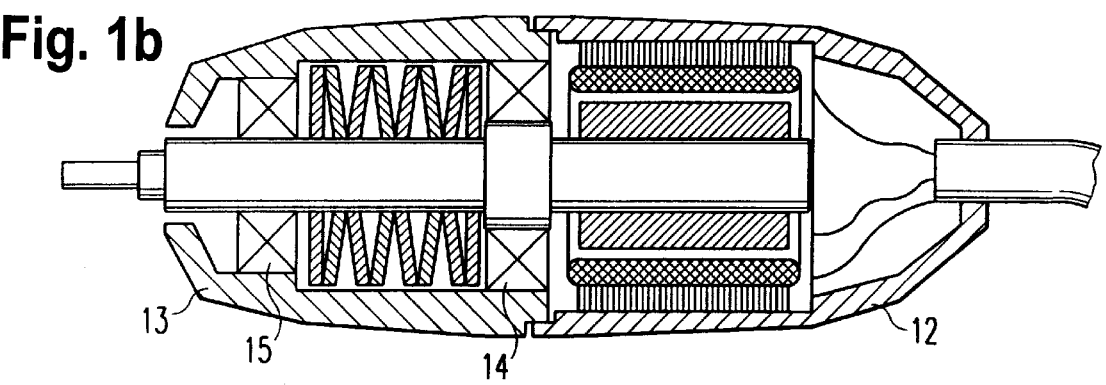

FIG. 1b shows a first variant of the motorised handpiece illustrated in FIG. 1a. As in FIG. 1a, the motor is again accommodated in the handpiece part 12 and the clamping mechanism in the handpiece part 13, the motor and the clamping mechanism being fitted onto the same shaft. In contrast to FIG. 1a, however, both ball bearings 14, 15 are arranged in the handpiece part 13 which is associated with the clamping mechanism. More particularly, the two ball bearings 14, 15 are arranged at opposite end sections of the handpiece part 13, the spring of the clamping mechanism being accommodated between the two ball bearings 14, 15. The drive shaft with the rotor magnet fitted thereon projects freely into the stator winding of the d.c. motor and according to FIG. 1b is not supported in the housing part 12 by a further support bearing.

Figure 1C:
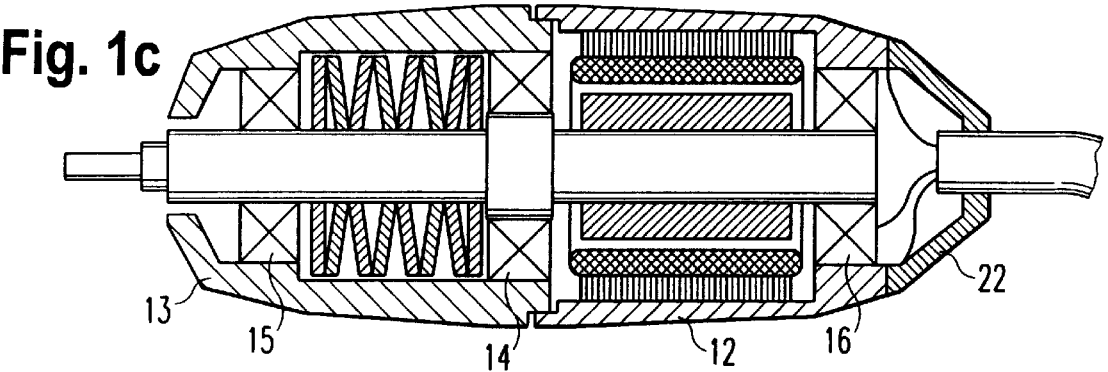
Figure 1D:
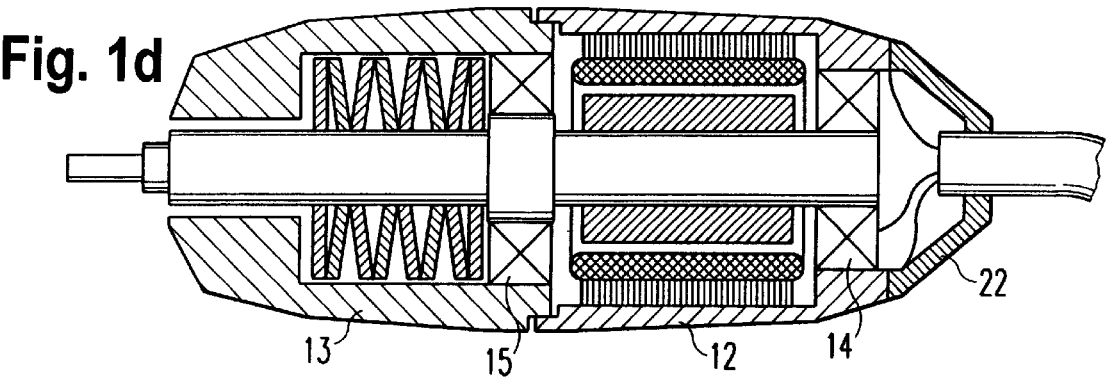

FIGS. 1c and 1d show further variants of the first embodiment according to the invention. The motorised handpiece according to FIG. 1c corresponds to the variant illustrated in FIG. 1b, although a third ball bearing 16 is additionally provided at the supply line end of the handpiece part 12. As in FIG. 1a, the handpiece part 12 again comprises a removable cover, so that the third ball bearing 16 is also easily accessible from the outside. The variant shown in FIG. 1d is based on the motorised handpiece illustrated in FIG. 1a, a ball bearing 14, 15 again being provided in the handpiece part 12 facing the electromotor and the handpiece part 13 associated with the clamping mechanism respectively. Whilst the first ball bearing 14 is accommodated at the supply line end of the handpiece part 12 as in FIG. 1a, the ball bearing 15 is now disposed at the end of the handpiece part 13 lying opposite the handpiece part 12. Also provided in FIG. 1d is a removable cover 22, so that the ball bearing 14 can be simply replaced.

FIGS. 2a–2d show different variants of a second embodiment of the invention. This second embodiment essentially corresponds to the first embodiment, although in contrast to FIG. 1 the clamping mechanism or the spring 7 of this clamping mechanism is accommodated in the handpiece part on the supply line side, whilst the collector-free d.c. motor is arranged in the housing part on the tool side.

Figure 2A:
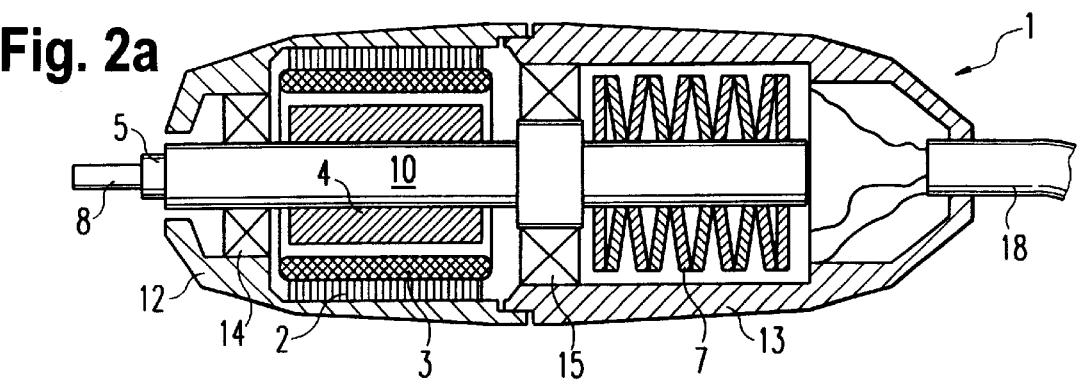
FIGS. 2a–2d show different variants of a second embodiment of the motorised handpiece according to the invention.

FIG. 2a shows the embodiment corresponding to the variant illustrated in FIG. 1d. The handpiece part 13, in which the clamping mechanism or the spring 7 of the clamping mechanism is accommodated, comprises an opening at one end, into which the supply line 18 projects, which supplies the stator winding 3 of the collector-free d.c. motor with current if the handpiece part 12 is coupled to the handpiece part 13. The actuating mechanism of the clamping system explained with the aid of FIG. 5a, which as a result of a rotation of the two housing parts 12 and 13 relative to one another causes the sleeve-shaped, slotted clamping jaw 5 to be displaced into the motorised handpiece 1 and to be correspondingly compressed, is disposed together with the spring 7 in the handpiece part 13. The clamping mechanism is again connected to the d.c. motor via a single shaft 10, which is integrally formed and is merely rotatably mounted at two bearing sites 14, 15. In this respect, one ball bearing 14 is disposed at the tool end of the handpiece part 12, whilst the other ball bearing 15 is disposed at the end section of the handpiece part 13 facing the handpiece part 12.

Figure 2B:
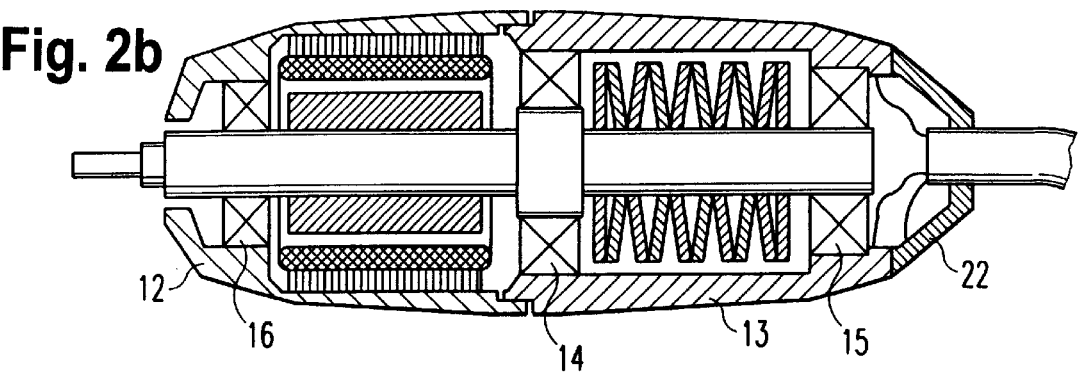

FIG. 2b shows a variant of the motorised handpiece according to the present invention illustrated in FIG. 2a, the motorised handpiece illustrated in FIG. 2b corresponding to the design illustrated in FIG. 1c, i.e. in addition to the ball bearings 14, 15, a third ball bearing 16 is provided for supporting the drive shaft 10. Since the arrangement of the d.c. motor and the clamping mechanism is reversed in the embodiments according to FIG. 2 as compared with the embodiments of FIG. 1, according to FIG. 2b the third ball bearing 16 is disposed at the tool end of the handpiece part 12. According to FIG. 2b, the ball bearing 15 is arranged at the supply line end of the handpiece part 13. For this reason, the handpiece part 13 comprises a removable cover 22, so that the ball bearing 15 can be easily accessed and replaced from the supply line side.

Figure 2C:
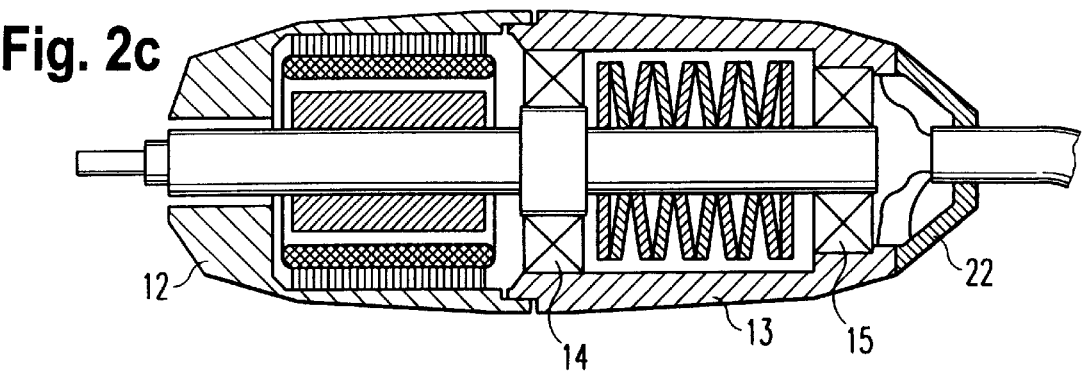
Figure 2D:
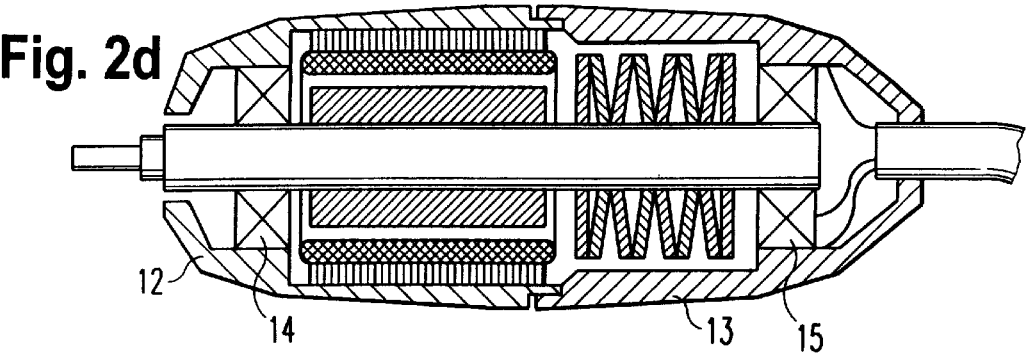

FIGS. 2c and FIG. 2d show arrangements of the second embodiment of the motorised handpiece according to the invention which correspond to the arrangements illustrated in FIGS. 1b and 1a respectively, although again the arrangement of the d.c. motor and the clamping mechanism is reversed as compared with FIG. 1, i.e. the clamping mechanism is located in each case in the handpiece part which is connected to the supply line 18, whilst the d.c. motor is accommodated in the handpiece part in which the tool 8 is clamped. In the variant according to FIG. 2c, the two ball bearings 14 and 15 are each accommodated in the handpiece part 13 at opposite ends thereof, so that the drive shaft projects freely into the stator winding of the d.c. motor of the handpiece part 12. In contrast, according to FIG. 2d, the two ball bearings 14 and 15 are accommodated at the respective outer ends of the handpiece parts 12 and 13, which results in maximum vibration rigidity of the drive shaft.

FIGS. 3a–3e show different variants of a motorised handpiece according to a third embodiment of the invention.

The variants illustrated in FIGS. 3a–3e essentially correspond to the variants illustrated in FIGS. 1a–1d, although according to the third embodiment of the invention, in contrast to FIG. 1, the rotor magnet 4 is accommodated in a cavity in the drive shaft 10.

Figure 3A:
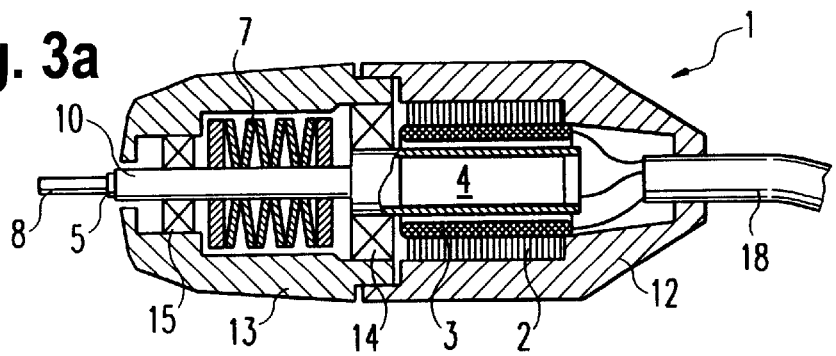
FIGS. 3a–3e show different variants of a third embodiment of the motorised handpiece according to the invention.
Figure 3B:
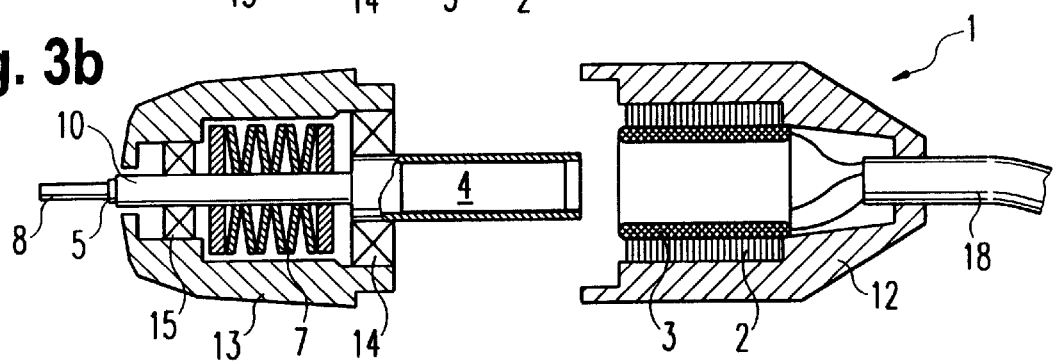

FIG. 3a shows a first variant of the third embodiment of the present invention in its assembled state, i.e. in a state where the two handpiece parts 12 and 13 are coupled together, for example screwed together, whilst FIG. 3b shows the corresponding variant with the handpiece parts 12 and 13 separated. It can be seen in particular from FIG. 3b that the drive shaft 10 projects freely from the handpiece part 13 and is held by two ball bearings 14 and 15 in the handpiece part 13, the section of the drive shaft 10 in which the rotor magnet 4 is accommodated being introduced into the stator winding 3 of the collector-free d.c. motor by joining the two handpiece parts 12 and 13. The stator winding 3 is supplied with current via the supply line 18, so that the rotor magnet 4, which is accommodated in a force-locking manner within the drive shaft 10, is set in rotation and the drive shaft 10 is simultaneously driven. The clamping mechanism can be constructed in the same manner as in the motorised handpieces illustrated in FIGS. 1, 2 and 5a.

Figure 3C:
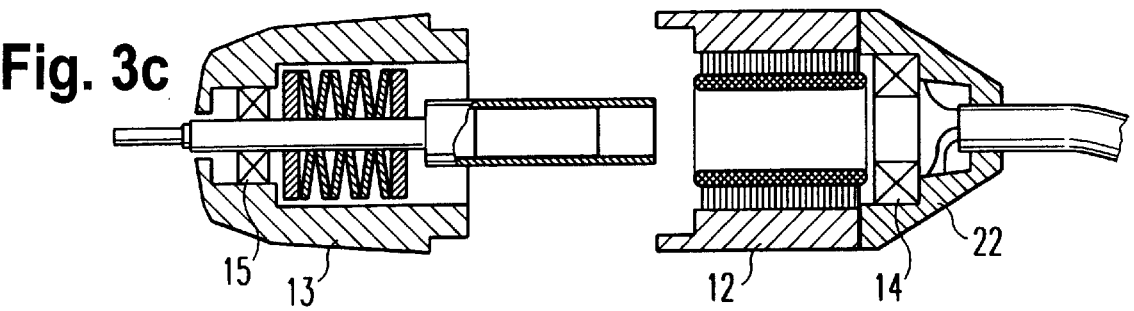

FIG. 3c shows a variant of the third embodiment according to the invention, the two ball bearings 14 and 15 being arranged in the same manner as in FIG. 1a, i.e. a ball bearing is arranged at the outer ends of the handpiece parts 12 and 13 respectively. As shown in FIG. 3c, the ball bearing 14 arranged at the supply line end can also be accommodated in the removable cover 22, so that easy accessibility of the ball bearing 14 is also ensured in this case.

Figure 3D:
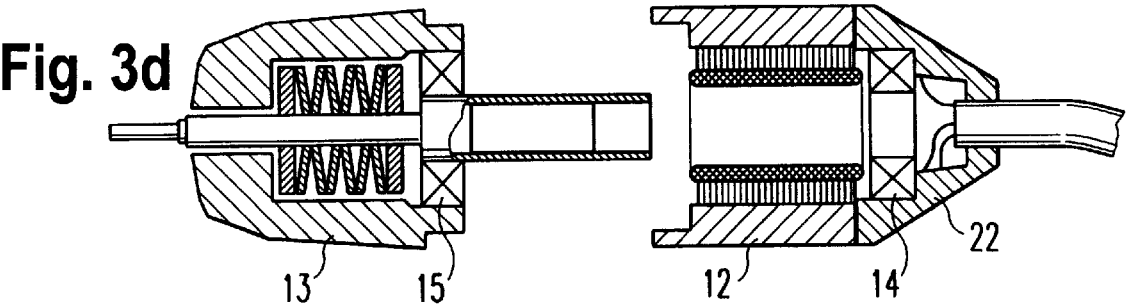
Figure 3E:
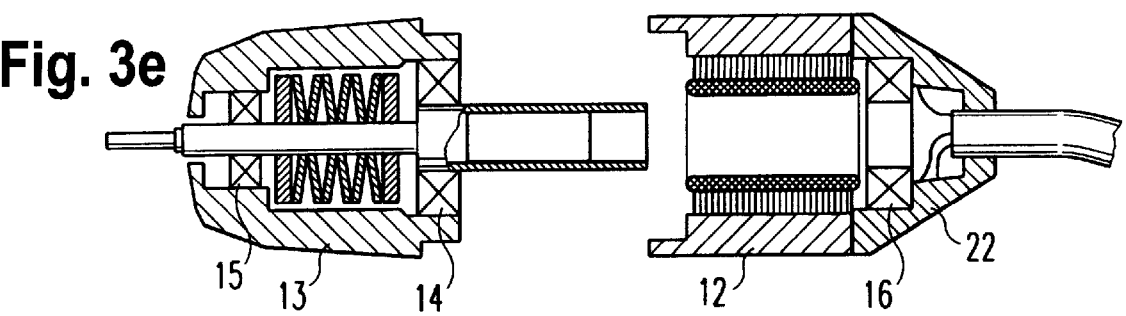

FIGS. 3d and 3e show variants of the third embodiment according to the invention, the arrangement of the ball bearings corresponding to the ball bearing arrangement illustrated in FIGS. 1d and 1c respectively. Both in FIG. 3d and in FIG. 3e, the ball bearing 14 or 16 on the supply line side is accommodated in the removable cover 22 of the handpiece part 12. Whilst only two ball bearings 14, 15 are used according to the variant illustrated in FIG. 3d, according to FIG. 3e the drive shaft is supported by a total of three ball bearings 14, 15, 16.

Finally, it should be noted that the invention can be applied to both operating handpieces used by dental technicians and treatment handpieces used by dentists. However, treatment handpieces used by dentists are often angled in design, so that the integral construction of the shaft proposed according to the invention is only applicable in this case to the core region of a dental treatment handpiece of this type.

Figure 4:
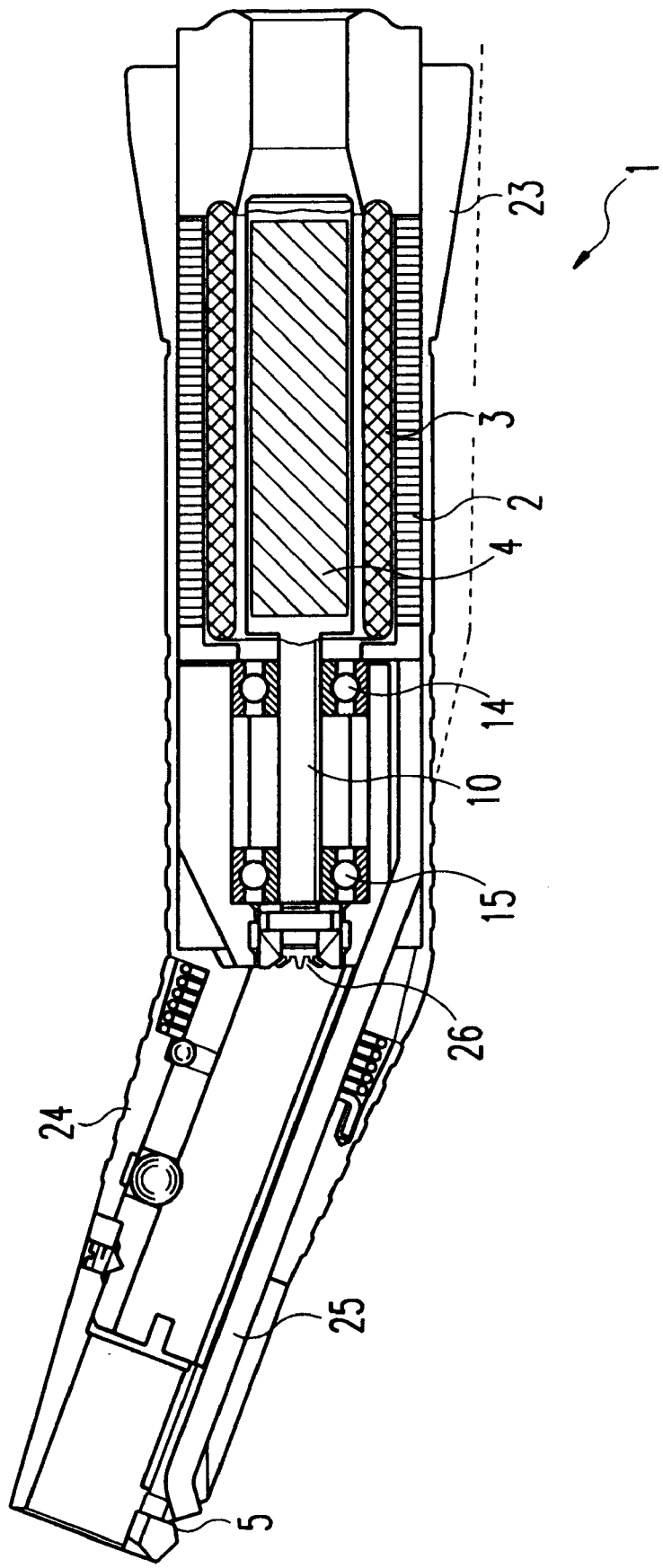
FIG. 4 shows a third embodiment of the motorised handpiece according to the invention.

FIG. 4 shows an example of a motorised handpiece 1 of this type according to the invention with a first housing section 23 and an angled second housing section 24. The motor 2–4 is accommodated in the first housing section 23, whilst a coupling mechanism 5 of optional design for receiving a (dental) tool is provided in the second housing section 24. In principle, this coupling mechanism can be formed in a similar manner to the preceding embodiments by a rapid clamping mechanism, it being possible to automatically clamp a tool, for example by rotating the second housing section 24. As regards further details of the method of operation and/or the design of a rapid clamping mechanism of this type, reference is made at this point to the description of the preceding embodiments.

On account of the angled construction of the motorised handpiece shown in FIG. 4, it is necessary to couple a further shaft (not shown) to the integrally formed drive shaft arrangement 10 arranged in the straight housing section 23 in the region of the angle, for example by means of a gearing 26. Accordingly, according to the present invention this integrally formed shaft 10 in the core region of the motorised handpiece 1 supports the motor or the rotor magnet 4 thereof on the one hand and the gearing 26 on the other hand and is again mounted in the motorised handpiece 1 via two ball bearings 14, 15.

The motorised handpiece 1 shown in FIG. 4 preferably comprises separation points such that the two ball bearings 14, 15 are easily accessible for replacement when the handpiece is divided. As shown in FIG. 4, the motorised handpiece 1 also comprises a duct 25 for dental purposes, in order to supply a treatment site with light, spray air or spray water, for example.

What is claimed is:

1. A motorized handpiece for driving a tool which can be coupled to the motorized handpiece, comprising:

an electric motor including a supply line for receiving electrical current;

a clamping mechanism including an elastic member for clamping a tool in a force-locking manner;

a shaft arrangement for transmitting rotary movement of the motor to the clamping mechanism, and hence, to a tool retained with the clamping mechanism, the shaft arrangement comprising an integrally formed shaft on which the motor and the clamping mechanism are arranged;

a first handpiece part and a second handpiece part, the motor and supply line being arranged in the first handpiece part and the elastic member being arranged in the second handpiece part, the elastic member being adapted to impart a tool retaining force to the clamping mechanism; and wherein the shaft is mounted at first and second bearing sites within the second handpiece part and respectively disposed at opposing ends of the second handpiece part, and the shaft including a shaft section extending unsupported from the second bearing site and into a stator of the motor.

2. The motorized handpiece of claim 1, wherein the first handpiece part can be coupled to the second handpiece part, and with the first handpiece part coupled to the second handpiece part, a tool located in the clamping mechanism is clamped in a force-locking manner within the clamping mechanism by the tool retaining force imparted by the elastic member.

3. The motorized handpiece of claim 2, wherein the elastic member comprises one of a spiral spring and a cup spring, and with the first handpiece part coupled to the second handpiece part, the elastic member is compressed for imparting the tool retaining force.

4. The motorized handpiece of claim 1, wherein the motor is a collector-free direct current motor with a stator winding and a rotor magnet, the stator winding being disposed in the first handpiece part and the rotor magnet being fitted to the shaft section such that rotary movement of the rotor magnet is transmitted to the shaft arrangement.

5. The motorized handpiece of claim 1, further comprising a removable cover coupled to a supply line end of the motorized handpiece, the supply line being introduced to the motor through the removable cover.

6. The motorized handpiece of claim 1, further comprising a ball bearing at each of the first bearing site and the second bearing site.

7. The motorized handpiece of claim 1, wherein the motorized handpiece is formed as a treatment handpiece for use in dentistry.

8. A motorized handpiece for driving a tool which can be coupled to the motorized handpiece, comprising:

an angled housing comprising a first housing section and a second housing section, the second housing section being arranged at an angle to the first housing section;

a motor disposed within the first housing section;

a coupling mechanism disposed within the second housing section, the coupling mechanism being adapted to receive and retain a tool;

a shaft arrangement for transmitting rotary movement of the motor to the coupling mechanism, and hence to a tool retained within the coupling mechanism, the shaft arrangement comprising a first shaft portion and a second shaft portion, the first and second shaft portions being coupled by a mechanical transmission mechanism;

the second shaft portion being rotatably supported in the second housing section; and wherein the first shaft portion is rotatably supported within the first housing section by a first bearing and a second bearing, and the first shaft portion is formed to include an extension portion with the extension portion extending into the motor in a cantilevered manner for coupling the motor to the shaft arrangement.

9. A motorized handpiece as in claim 8, wherein the first housing is rotatable with respect to the second housing for engaging the coupling mechanism with a tool to be retained therein.

10. A motorized handpiece as in claim 8, wherein the motor is an electric motor.

11. A motorized handpiece as in claim 8, wherein the motorized handpiece is formed as a treatment handpiece for use in dentistry.

* * * * *